(12) United States Patent
Weiler

(10) Patent No.: US 8,808,193 B2
(45) Date of Patent: Aug. 19, 2014

(54) REGIONAL OXYGEN UPTAKE/PERFUSION MEASURING DEVICE AND METHOD

(75) Inventor: Norbert Weiler, Heikendorf (DE)

(73) Assignee: Carefusion 207, Inc., San Diego, CA (US)

(*) Notice: Subject to any disclaimer, the term of this patent is extended or adjusted under 35 U.S.C. 154(b) by 1126 days.

(21) Appl. No.: 12/206,532

(22) Filed: Sep. 8, 2008

(65) Prior Publication Data

US 2009/0118634 A1     May 7, 2009

Related U.S. Application Data

(60) Provisional application No. 60/960,015, filed on Sep. 11, 2007.

(51) Int. Cl.
*A61B 5/08* (2006.01)

(52) U.S. Cl.
USPC ............................ 600/529; 600/536; 600/547

(58) Field of Classification Search
USPC .................... 600/529, 532, 538, 547, 536
See application file for complete search history.

(56) References Cited

U.S. PATENT DOCUMENTS

| | | | |
|---|---|---|---|
| 5,311,878 A | 5/1994 | Brown et al. | |
| 6,015,389 A | 1/2000 | Brown | |
| 6,277,080 B1* | 8/2001 | Nissila et al. | 600/508 |
| 6,370,415 B1 | 4/2002 | Weiler et al. | |
| 6,595,211 B2 | 7/2003 | Weiler et al. | |
| 6,650,924 B2 | 11/2003 | Kuth et al. | |
| 6,915,151 B2 | 7/2005 | Baumgardner et al. | |
| 7,162,296 B2 | 1/2007 | Leonhardt et al. | |
| 7,225,022 B2* | 5/2007 | Anderson et al. | 607/18 |
| 2003/0216664 A1 | 11/2003 | Suarez | |
| 2004/0249301 A1 | 12/2004 | Stenqvist | |
| 2006/0260611 A1 | 11/2006 | Garber et al. | |
| 2007/0167758 A1* | 7/2007 | Costello | 600/437 |

OTHER PUBLICATIONS

Wolf, G et al. "Noninvasive assessment of lung volume: Respiratory inductance plethysmography and electrical impedance tomography." Crit Care Med, 2005, vol. 33, No. 3, pp. S163-S169.*
Office Action, CN Application No. 200880106622.5, mailed May 4, 2011, 10 pages.
Frerichs, Inez et al., "Regional Lung Perfusion as Determined by Electrical Impedance Tomography in Comparison With Electron Beam CT Imaging," IEE Transactions on Medical Imaging, vol. 21, No. 6. Jun. 2002.
Smulders, Leo et al., "EIT measurements and tic prediction of lung volume," Engineering in Medicine and Biology Society, 1988, Proceedings of the Annual International Conference of the IEEE, New York, 1756-1757, Oct. 29, 1992.

(Continued)

*Primary Examiner* — Navin Natnithithadha
*Assistant Examiner* — Etsub Berhanu
(74) *Attorney, Agent, or Firm* — McDermott Will & Emery LLP

(57) ABSTRACT

To assess regional oxygen uptake and/or perfusion in a patient, a volume of air inhaled by the patient is determined and, according to a method of electrical impedance tomography, a first regional lung volume is measured at a first time point of a breathold procedure. The first regional lung volume is compared to a second regional lung volume at a second time point of the breathold procedure.

6 Claims, 3 Drawing Sheets

(56) References Cited

OTHER PUBLICATIONS

Brunner, Patricia et al., "Imaging of local lung ventilation under different gravitational conditions with electrical impedance tomography," ACTA Astronautica 60 (2007). 281-284.

Woo, Eung Je et al., "Measuring Lung Resitivity Using Electrical Impedance Tomography," IEEE Transactions on Biomedical Engineering, New York, vol. 39, Jul. 1992, No, 7, 756-760.

Extended European Search Report for EP Patent Application No. 08799358 dated May 24, 2013.

* cited by examiner

REGIONAL OXYGEN UPTAKE/PERFUSION MEASURING DEVICE AND METHOD

CROSS REFERENCE TO RELATED APPLICATIONS

This Non-Provisional application claims priority to U.S. Provisional Application Ser. No. 60/960,015, filed on Sep. 11, 2007, titled "REGIONAL OXYGEN UPTAKE/PERFUSION MEASURING DEVICE AND METHOD," the disclosure of which is incorporated herein by reference in the entirety

FIELD OF THE INVENTION

The present invention generally relates to measurement of oxygen uptake and/or perfusion in the lungs of a patient. More particularly, the present invention pertains to determining an amount of oxygen uptake and/or perfusion in regions of the lungs with an electrical impedance tomography device and the method of doing so.

BACKGROUND OF THE INVENTION

Electrical impedance tomography (EIT) is a known medical imaging technique in which an image of the conductivity or permittivity of part of a patient is inferred from electrical measurements sensed at the surface of the patient. Typically, conducting electrodes are attached to the skin of the patient in a pattern that encircles an area of interest. Small alternating currents on the order of a few nano-amperes (nA) to several mili-amperes (mA) are applied to some or all of the electrodes at a frequency that is generally in the kilo-Hertz (kHz) range. The resulting electrical potentials are measured, and the process repeated for numerous different configurations of applied current.

SUMMARY OF THE INVENTION

The present invention provides, in some embodiments, a device and method of determining the regional uptake of oxygen in the lungs of a patient. In addition, posture dependent regional oxygen uptake and/or perfusion may be determined by various embodiments of the invention.

An embodiment of the present invention pertains to a method of assessing regional oxygen uptake and/or perfusion in a patient. In this, a volume of air inhaled by the patient is determined and, according to a method of electrical impedance tomography, a first regional lung volume is measured at a first time point of a breathold procedure. The first regional lung volume is compared to a second regional lung volume at a second time point of the breathold procedure.

Another embodiment of the present invention relates to a device to assess regional oxygen uptake and/or perfusion in a patient. The device includes an electrical impedance tomography device configured to measure a first regional lung volume at a first time point of a breathold procedure. In addition, the electrical impedance tomography device is configured to compare the first regional lung volume to a second regional lung volume at a second time point of the breathold procedure.

Yet another embodiment of the present invention pertains to a system to assess regional oxygen uptake and/or perfusion in a patient, the system includes an electrical impedance tomography device, a signal processor, and a display. The electrical impedance tomography device is configured to sense the patient and forward signals in response to sensing the patient. The signal processor is configured to receive the signals. The signal processor includes an algorithm configured to determine a first regional lung volume at a first time point of a breathold procedure in response to the signals and compare the first regional lung volume to a second regional lung volume at a second time point of the breathold procedure. The algorithm is configured to determine a regional oxygen uptake and/or perfusion in response to the comparison. The display displays the regional oxygen uptake and/or perfusion.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Figure 1:
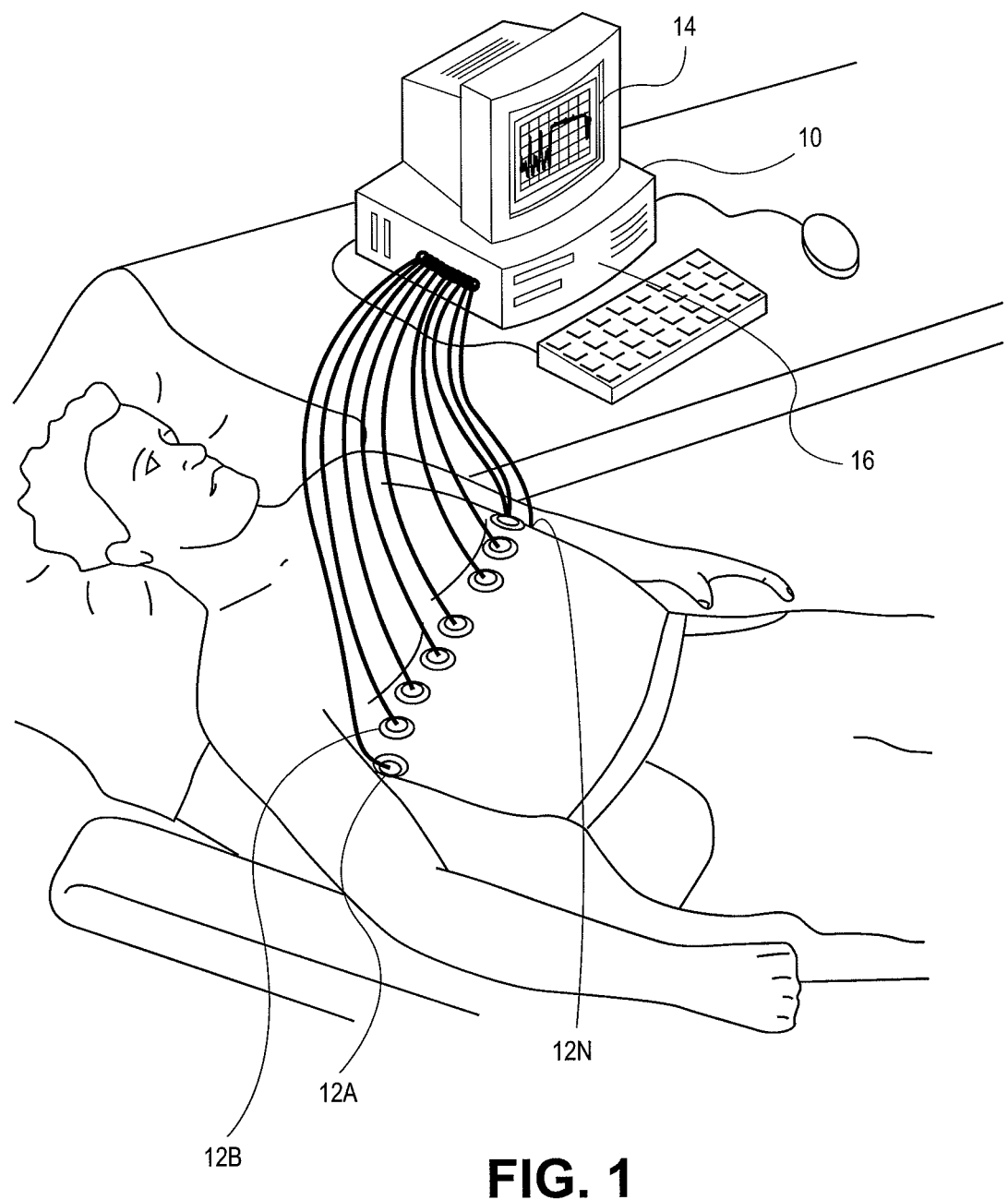
FIG. 1 is perspective view of a patient being scanned by a suitable electrical impedance tomography (EIT) device according to an embodiment of the invention.

of a left lung oxygen uptake for a normal patient in a left lateral posture according to an embodiment of the invention.

DETAILED DESCRIPTION OF THE PREFERRED EMBODIMENT

Various embodiments of the invention utilize electrical impedance tomography (EIT) technology to sense and analyze regional gas contents of the lungs. Based on this analysis, regional uptake of oxygen is calculated and regional pulmonary perfusion is deduced. It is an advantage of at least one embodiment that a non-invasive, real-time, patient pulmonary perfusion may be deduced for regions of the patient's lungs.

It is an advantage that embodiments of the invention may be utilized to assess regional distribution of ventilation and, furthermore, to assess regional perfusion in the lungs of a patient. Moreover, it is an advantage that embodiments of the invention may be utilized to match distribution of ventilation and perfusion. Stated in another manner, the regional perfusion of a patient may be assessed. In a particular example, the regional perfusion capacity or regional ability of a patients lungs may be assessed or determined and the patient's posture may be adjusted to optimize ventilation.

Oxygen uptake in the lung depends on ventilation and perfusion. It is known, that in Acute Lung Injury, the disease process is distributed largely inhomogeneously in the lung. Hypoxia due to ventilation-perfusion mismatch is the most severe complication in these patients. Therapy depends primarily upon ventilatory strategies (PEEP, I:E-ratio, assisted ventilation allowing spontaneous breathing, etc.) to improve ventilation-perfusion ratio without damaging the lung. Currently, it is not possible to assess the effects of these strategies on regional ventilation and perfusion at the bedside.

Embodiments of the present invention have been shown to provide a system, device and method of assessing the effects of ventilation strategies on regional ventilation and perfusion in real-time and at the bedside of the patient. The principal idea in assessing regional perfusion is to use local oxygen uptake as an indicator for local perfusion (i.e., As blood passes alveoli, it extracts oxygen from them). Therefore if oxygen uptake is reduced or halted, this condition may be attributed to a reduced or halted blood flow). As shown and described hereinabove, oxygen uptake can be measured during a period of breathold as regional volume change. To quantify oxygen uptake, the change in the relative impedance change may be calibrated in any suitable manner such as, for example, by spirometry, inhalation or exhalation of a known gas volume. In a particular example, a known ventilator may be utilized to deliver a breath to the patient or the patient breath volume may by measured with any suitable flow sensors. Knowing regional oxygen uptake, local blood flow may be calculated based upon mixed venous oxygen saturation of hemoglobin and the concentration of hemoglobin. Alternatively, these values may be assumed for relative evaluations. From these two values the amount of oxygen per ml blood up to a saturation of 100 percent may be calculated. It can be assumed that at higher inspiratory oxygen concentrations (In a preferred embodiment 100 percent oxygen is utilized) the blood flowing through ventilated lung region is completely saturated after leaving the lung.

As an example of the calculation of blood flow for the whole lung: Assumed mixed venous saturation 70%, Hb concentration 12 g/dl oxygen uptake 200 ml/min O2-uptake ml/min; 0.12 g/ml (Hb-concentration)×1.39 ml/g (Hemoglobin binding factor)×(1-0.7) (difference in saturation). In this example, blood flow is 4000 ml/min. To assess the ventilation perfusion ratio, the patient is ventilated at 100% oxygen for several minutes. The global EIT ventilation may be scaled or calibrated based upon the measured global volume from the flow sensor or ventilator. From this scaled global EIT ventilation, the regional ventilation in ml/min may be calculated. An end-inspiratory breathold may be performed in an example. In other examples, a breathold at substantially any point may be suitable. From this breathold we measure oxygen uptake of the same region based upon a decrease in lung volume as sensed by a decrease in impedance. It is a particular advantage of embodiments of the invention that regional ventilation/perfusion ratio may be calculated based upon the respective contribution to impedance from the individual regions. Studies performed on lung healthy spontaneously breathing subjects easily demonstrated the effects of posture on regional oxygen uptake and consequently perfusion.

An embodiment of the invention will now be described with reference to the drawing figures, in which like reference numerals refer to like parts throughout. As shown in FIG. 1, an EIT device 10 includes a series of sensors 12a-12n and a computing/displaying unit 14. The sensors 12a-12n may be arranged about the patient and controlled to determine the impedance of the patient at the sensors 12a-12n. In a particular example, the EIT device 10 includes 16 sensors 12a-12n and is configured to generate and analyze multi-frequency signals. However, in other examples, suitable EIT devices may include fewer or greater sensors 12a-12n and may or may not generate and analyze multi-frequency signals. As is generally known, during an EIT procedure, one or more of the sensors 12a-12n generate a signal and the remainder of the sensors 12a-12n sense an impedance to the signal. The fluids and tissues of the body offer varying levels of impedance to these signals and air offers high impedance to the signals. Typically, a multitude of such signals are utilized to generate sufficient data to image the patient. In this manner, the volume of air in the patient may be determined.

According to an embodiment of the invention, the EIT device 10 includes an algorithm 16 to evaluate the EIT data for measurement of regional oxygen uptake. The algorithm 16 is configured to utilize measured breathing volume to scale the EIT signals for volume change. The algorithm 16 is further configured to utilize the EIT measured reduction in volume during a breathold to calculate the oxygen uptake from perfusion to a region of the lung. That is, the patient's breathing is stopped or the patient is instructed to stop or hold their breath for a suitable length of time. Examples of suitable breathold durations include 60 seconds, 100 seconds, 120 seconds, and the like. The exact length of time is unimportant. During the breathold procedure, any reduction of lung volume may be attributed to the uptake of oxygen. It is an advantage of embodiments of the invention that the uptake of oxygen may be determined for individual regions of the lungs as well as for global oxygen uptake. Depending upon the placement of the sensors 12a-12n, the regions may include right/left lung, upper/middle/lower lung, and the like. In a particular example, the EIT device 10 shown in FIG. 1 may be utilized to determine the oxygen uptake for the left and right lungs.

Figure 2:
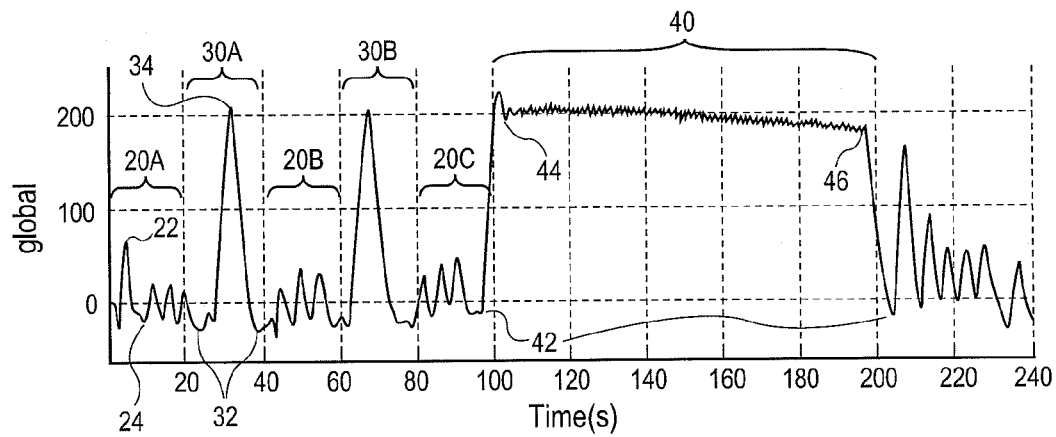
FIG. 2 is an example of a graph of time in seconds (abscissa) as it affects the transfer impedance in ohms (ordinate) of a global lung oxygen uptake for a normal patient in a supine position according to an embodiment of the invention.

FIG. 2 is an example of a graph of time in seconds (abscissa) as it affects the transfer impedance in ohms (ordinate) of a global lung oxygen uptake for a normal patient in a supine position according to an embodiment of the invention. As shown in FIG. 2, the tracing begins with a phase of spontaneous or tidal breathing 20a. In particular, four (4) breaths are shown in tidal breathing 20a punctuated by inhalation 22 and exhalation 24 events. The tracing goes on to show a vital capacity (VC) maneuver 30a that is initiated at a full exhalation 32 continues through a full inhalation 34 and terminates at a full exhalation 34. Following a tidal breathing 20b, VC maneuver 30b, and tidal breathing 20c, an apneic phase 40 is initiated following a full exhalation 42 and then a full inhalation 44. The apneic phase 40 includes a breathold that is performed for a suitable duration. Of particular note, the apneic phase 40 is characterized by a breathold maneuver that proceeds from point 44 to point 46 on the tracing. The duration of this event is approximately 100 seconds. During this time, the impedance, and therefore the lung volume, is shown to decrease. This decrease in volume is attributable to the uptake of oxygen in the lungs. Oxygen uptake itself is an indicator of lung perfusion and therefore blood flow therethrough.

The algorithm 16 determines the change in volume of the lungs from point 44 to point 46 on the tracing and calculates the oxygen uptake based on the change in volume. In the particular example shown in FIG. 2, the vital capacity for the patient is 5.3 liters (l), oxygen uptake is 393 milliliters (ml) per minute (ml/min), and the perfusion is (Sv: 70%), Hb: 12 g/dl): 7.8 l per minute (l/min).

Figure 3:
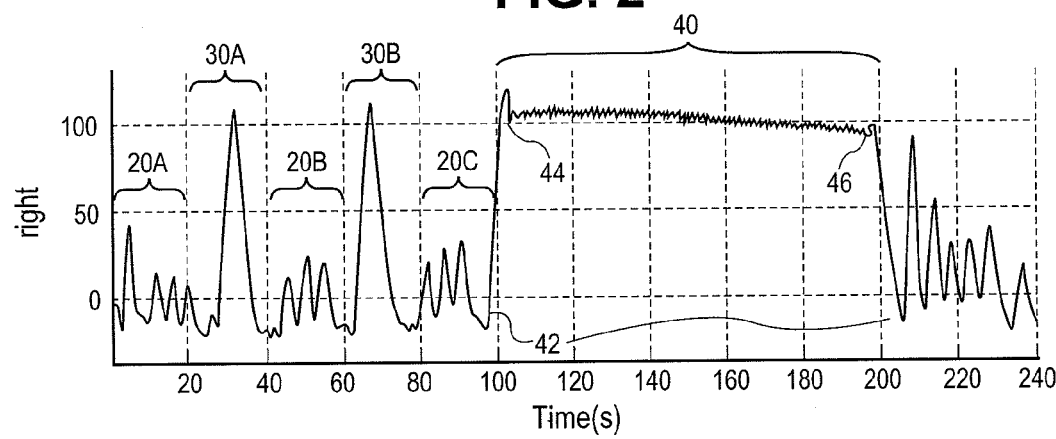
FIG. 3 is an example of a graph of time in seconds (abscissa) as it affects the transfer impedance in ohms (ordinate) of a right lung oxygen uptake for a normal patient in a supine position according to an embodiment of the invention.

FIG. 3 is an example of a graph of time in seconds (abscissa) as it affects the transfer impedance in ohms (ordinate) of a right lung oxygen uptake for a normal patient in a supine position according to an embodiment of the invention. As shown in FIG. 3, the tracing follows a similar pattern as compared to the tracing of FIG. 2. In particular, the tracing shown in FIG. 3 includes the tidal breathing phases 20a-20c, the VC maneuver 30a and 30b, and the apneic phase 40. Of note, the tracing shows that the right lung accounts for slightly greater than 50% of the global oxygen uptake for the lungs. Specifically, the oxygen uptake is calculated to be 226 ml/min and the perfusion (Sv: 70%, Hb: 12 g/dl): is 4.5 l/min.

Figure 4:
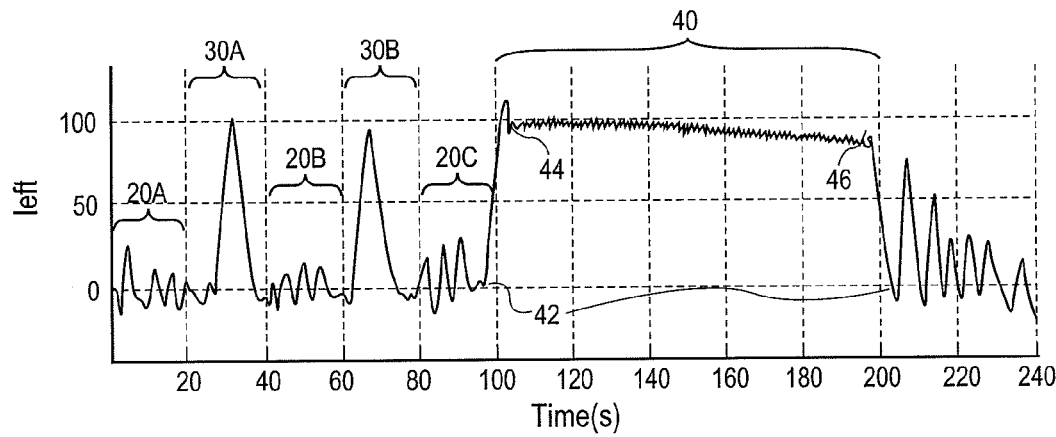
FIG. 4 is an example of a graph of time in seconds (abscissa) as it affects the transfer impedance in ohms (ordinate) of a left lung oxygen uptake for a normal patient in a supine position according to an embodiment of the invention.

FIG. 4 is an example of a graph of time in seconds (abscissa) as it affects the transfer impedance in ohms (ordinate) of a left lung oxygen uptake for a normal patient in a supine position according to an embodiment of the invention. As shown in FIG. 4, the tracing follows a similar pattern as compared to the tracing of FIGS. 2 and 3. Again, the tracing shown in FIG. 4 includes the tidal breathing phases 20a-20c, the VC maneuver 30a and 30b, and the apneic phase 40. Of note, the tracing shows that the left lung accounts for slightly less than 50% of the global oxygen uptake for the lungs. Specifically, the oxygen uptake is calculated to be 167 ml/min and the perfusion (Sv: 70%, Hb: 12 g/dl): is 3.3 l/min. This slightly reduced oxygen uptake for the left lung as compared with the right is consistent with the size discrepancy of the right verses left lung.

The tracings shown in FIGS. 2, 3, and 4 generally illustrate a normal or control condition of the lungs. By comparing these tracing to others, any differences noted can be utilized to diagnose a potential problem or disease condition in a patient. In addition, by performing these measurements at various patient positions, position dependent oxygen uptake and/or lung perfusion may be determined. In the following FIGS. 5, 6, and 7, a normal male subject is measured while in a left lateral posture.

Figure 5:
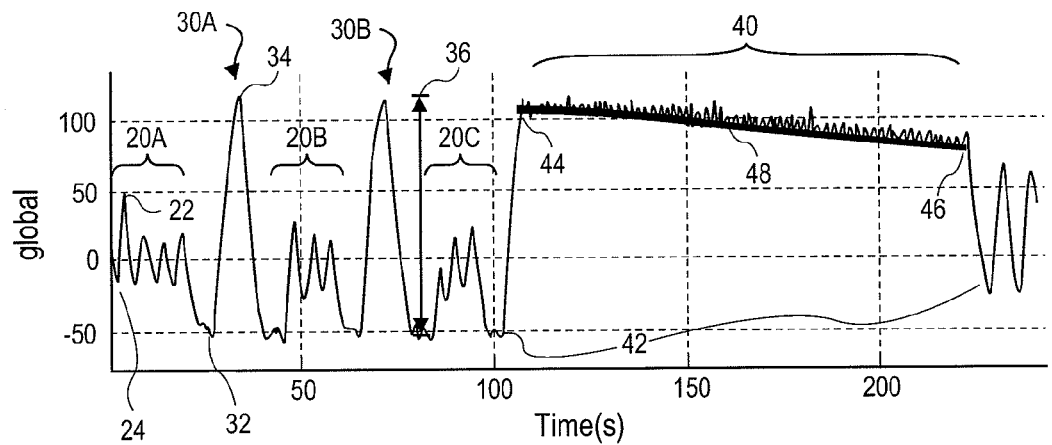
FIG. 5 is an example of a graph of time in seconds (abscissa) as it affects the transfer impedance in ohms (ordinate) of a global lung oxygen uptake for a normal patient in a left lateral posture according to an embodiment of the invention.

FIG. 5 is an example of a graph of time in seconds (abscissa) as it affects the transfer impedance in ohms (ordinate) of a global lung oxygen uptake for a normal patient in a left lateral posture according to an embodiment of the invention. As shown in FIG. 5, the tracing follows a similar pattern as compared to the tracing of FIG. 2. Again, the tracing shown in FIG. 5 includes the tidal breathing phases 20a-20c, the VC maneuver 30a and 30b, and the apneic phase 40. In addition, the FIG. 5 includes a volume calibration 36 calibrated during the VC maneuver 30b. According to various embodiments, the volume calibration 36 may be performed in any suitable manner such as, for example, via spirometry or other such pulmonary function procedure. The volume calibration may be performed at essentially any time during the procedure and need not be performed during a VC maneuver.

In another example, the volume calibration may be performed just prior to the apneic phase 40 starting at the full exhalation 42 and ending at the full inhalation 44. In addition, the test may be performed at substantially any breath point. That is, the apneic phase 40 may be performed at any breath point between the full exhalation 42 and the full inhalation 44. As such, the test may be performed on patients that are not capable or advised against performing a full inhalation maneuver.

Also shown in FIG. 5, the tracing includes a line 48 designating the slope of the tracing during the apneic phase 40. The line 48 lays along a calculated "best fit" as determined by the algorithm 16. In addition, other mathematical models for the rate of change in volume may be used by the algorithm. This line 48 generally shows the average decrease in volume in the lungs or region of the lungs during the apneic phase 40 and may be utilized to calculate the oxygen uptake. The values determined based on the volume calibration 36, and the tracing are as follows: Volume calibration is 5.4 l; Oxygen uptake is calculated to be 421 ml/min and the perfusion (Sv: 70%, Hb: 12 g/dl): is 8.4 l/min. When compared to the global values for a normal male in the supine position shown in FIG. 2, these values for FIG. 4 appear very similar. However, as shown in FIGS. 6 and 7, the regional or individual values for the right and left lungs are markedly different depending upon the posture.

Figure 6:
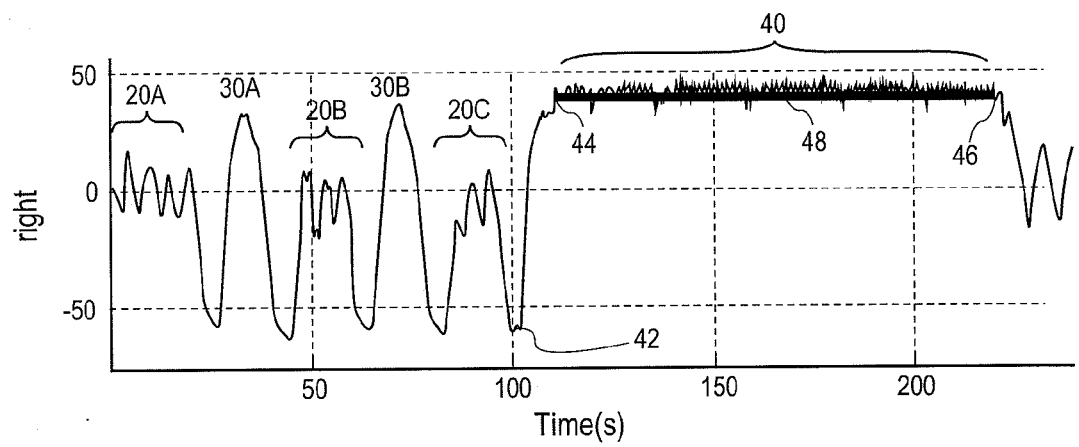
FIG. 6 is an example of a graph of time in seconds (abscissa) as it affects the transfer impedance in ohms (ordinate) of a right lung oxygen uptake for a normal patient in a left lateral posture according to an embodiment of the invention.

FIG. 6 is an example of a graph of time in seconds (abscissa) as it affects the transfer impedance in ohms (ordinate) of a right lung oxygen uptake for a normal patient in a left lateral posture according to an embodiment of the invention. As shown in FIG. 6, the tracing follows a pattern that is somewhat similar to the tracing of FIG. 5. For example, the tracing shown in FIG. 6 includes the tidal breathing phases 20a-20c, the VC maneuver 30a and 30b, and the apneic phase 40. The tracing of FIG. 6 also differs greatly from FIG. 5 with respect to the slope of the line 48. The nearly horizontal line 48 is indicative of a relatively low oxygen uptake. Specifically, the oxygen uptake is calculated to be 39 ml/min and the perfusion (Sv: 70%, Hb: 12 g/dl): is 0.8 l/min. This strongly reduced oxygen uptake is offset by a strong increase in oxygen uptake shown in FIG. 7. This phenomenon may be attributed in some degree to a gravitationally induced flow of blood into the lower (left) lung.

Figure 7:
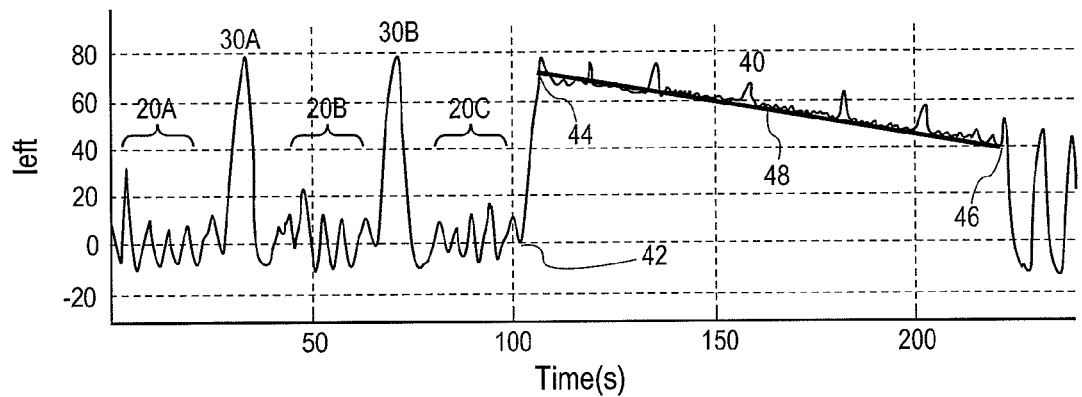
FIG. 7 is an example of a graph of time in seconds (abscissa) as it affects the transfer impedance in ohms (ordinate)

FIG. 7 is an example of a graph of time in seconds (abscissa) as it affects the transfer impedance in ohms (ordinate) of a left lung oxygen uptake for a normal patient in a left lateral posture according to an embodiment of the invention. As shown in FIG. 7, the tracing follows a pattern that is somewhat similar to the tracing of FIG. 5. For example, the tracing shown in FIG. 7 includes the tidal breathing phases 20a-20c, the VC maneuver 30a and 30b, and the apneic phase 40. Of note, the tracing of FIG. 7 differs greatly from the tracing FIG. 6 with respect to the slope of the line 48. The nearly horizontal line 48 of FIG. 6 is in marked contrast to the strongly sloping line 48 shown in FIG. 7. The line 48 in FIG. 7 is indicative of a relatively high oxygen uptake. Specifically, the oxygen uptake is calculated to be 382 ml/min and the perfusion (Sv: 70%, Hb: 12 g/dl): is 7.6 l/min. Again, this phenomenon may be attributed in some degree to a gravitationally induced flow of blood into the lower (left) lung.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device comprising:
   an electrical impedance tomography (EIT) device configured to measure a regional lung volume without use of a contrast marker,
   wherein the device is configured to:
      measure with the EIT a first regional lung volume at a first time point of a breathold procedure and at a second time point of the breathold procedure;
      determine a change in the first regional lung volume; and
      determine a first regional oxygen uptake based at least in part on the change in the first regional lung volume.

2. The device of claim 1, wherein the device is further configured to perform a volume calibration at a time outside of the breathold procedure.

3. The device of claim 1, wherein the device is further configured to measure with the EIT a second regional lung volume at the first and second time points of the breathold procedure and determine a change in the second regional lung volume.

4. The device of claim 3, wherein the device is further configured to determine a first regional oxygen uptake and a second regional oxygen uptake based at least in part on the respective changes in first and second regional lung volumes.

5. The device of claim 1, wherein the device is further configured to measure the first regional lung volume at the first and second time points of a breathold procedure performed at any breath point between a full exhalation and a full inhalation.

6. A method of determining regional oxygen uptake, the method comprising the steps of:
   measuring with an electrical impedance tomography (EIT) device, and without use of a contrast marker, a first regional lung volume at a first time point of a breathold procedure;
   measuring with the EIT device, and without use of a contrast marker, the first regional lung volume at a second time point of the breathold procedure;
   determining a change in the first regional lung volume; and
   determining a first regional oxygen uptake based at least in part on the change in first regional lung volume.

* * * * *